United States Patent
Ueda et al.

(10) Patent No.: US 10,308,612 B2
(45) Date of Patent: Jun. 4, 2019

(54) METHOD FOR PRODUCING 1-(ACYLOXY)ALKYL CARBAMATE DERIVATIVE

(71) Applicant: DAIICHI SANKYO COMPANY, LIMITED, Tokyo (JP)

(72) Inventors: Tsuyoshi Ueda, Kanagawa (JP); Yuzo Abe, Kanagawa (JP)

(73) Assignee: DAIICHI SANKYO COMPANY, LIMITED, Tokyo (JP)

( * ) Notice: Subject to any disclaimer, the term of this patent is extended or adjusted under 35 U.S.C. 154(b) by 0 days.

(21) Appl. No.: 15/739,361

(22) PCT Filed: Jun. 24, 2016

(86) PCT No.: PCT/JP2016/068796
§ 371 (c)(1),
(2) Date: Dec. 22, 2017

(87) PCT Pub. No.: WO2016/208709
PCT Pub. Date: Dec. 29, 2016

(65) Prior Publication Data
US 2018/0170880 A1    Jun. 21, 2018

(30) Foreign Application Priority Data
Jun. 26, 2015 (JP) ................................. 2015-129196

(51) Int. Cl.
| | | |
|---|---|---|
| *C07D 233/64* | (2006.01) | |
| *C07C 68/06* | (2006.01) | |
| *C07C 69/96* | (2006.01) | |
| *C12P 41/00* | (2006.01) | |
| *C07B 43/06* | (2006.01) | |
| *C12P 17/14* | (2006.01) | |
| *C07B 61/00* | (2006.01) | |

(52) U.S. Cl.
CPC ............ *C07D 233/64* (2013.01); *C07B 43/06* (2013.01); *C07C 68/06* (2013.01); *C07C 69/96* (2013.01); *C12P 17/14* (2013.01); *C12P 41/00* (2013.01); *C07B 61/00* (2013.01); *C07B 2200/13* (2013.01); *C12Y 301/01003* (2013.01)

(58) Field of Classification Search
CPC ....... C07D 233/64; C07B 43/06; C07C 68/06; C07C 69/96

USPC ........................................................ 544/262
See application file for complete search history.

(56) References Cited

U.S. PATENT DOCUMENTS

| | | |
|---|---|---|
| 4,916,230 A | 4/1990 | Alexander |
| 2013/0022587 A1 | 1/2013 | Nagata et al. |
| 2014/0243544 A1 | 8/2014 | Wang et al. |

FOREIGN PATENT DOCUMENTS

| | | |
|---|---|---|
| WO | WO 03/077902 A1 | 9/2003 |
| WO | WO 03/104184 A1 | 12/2003 |
| WO | WO 2005/010011 A2 | 2/2005 |
| WO | WO 2005/066122 A2 | 7/2005 |
| WO | WO 2010/017504 A1 | 2/2010 |
| WO | WO 2011/115064 A1 | 9/2011 |

OTHER PUBLICATIONS

Alexander et al., "(Acyloxy)alkyl Carbamates as Novel Bioreversible Prodrugs for Amines: Increased Permeation through Biological Membranes," *J. Med. Chem.*, (1988), 31(2):318-322.
Ashizawa, "Shio Kesshokei no Saitekika to Kesshoka Gijutsu," *Pharm. Tech. Japan*, (2002), 18(10):81-96, with English translation.
Hirayama (ed.), Yuki Kagobutsu Kessho Sakusei Handbook, Maruzen Co., Ltd., Jul. 25, 2008, pp. 57-84, with English translation.
Luo et al., "Fluorous Boc ($^F$Boc) Carbarnates: New Amine Protecting Groups for Use in Fluorous Synthesis," *J. Org. Chem.*, (2001), 66:4261-4266.
English Translation of International Search Report dated Sep. 20, 2016, in PCT Application No. PCT/JP2016/068796, 4 pages.
English Translation of Written Opinion dated Sep. 20, 2016, in PCT Application No. PCT/JP2016/068796, 7 pages.
English Translation of International Preliminary Report on Patentability dated Dec. 26, 2017, in PCT Application No. PCT/JP2016/068796, 8 pages.
Lin et al., "Mono and Bis Double Ester Prodrugs of Novel Aminomethyl-THF 1β-Methylcarbapenems," *Bioorganic & Medicinal Chemistry Letters*, (1997), 7(14):1811-1816.

*Primary Examiner* — Kahsay Habte
(74) *Attorney, Agent, or Firm* — Dorsey & Whitney LLP

(57) ABSTRACT

A method for producing a 1-(acyloxy)alkyl carbamate derivative (III), using a fluorous alkyl carbonate derivative (I), and a fluorous alkyl carbonate derivative (I) and a method for producing the same. In the formula, $R^1$ represents $C_1$-$C_4$ alkyl group or a $C_3$-$C_6$ cycloalkyl group, $R^2$ represents a $C_1$-$C_4$ alkyl group or a hydrogen atom, and A represents a fluorous alkyl group (wherein the fluorous alkyl group represents a $C_2$-$C_{11}$ alkyl group in which 40% or more of the hydrogen atoms are replaced by fluorine atoms).

14 Claims, 1 Drawing Sheet

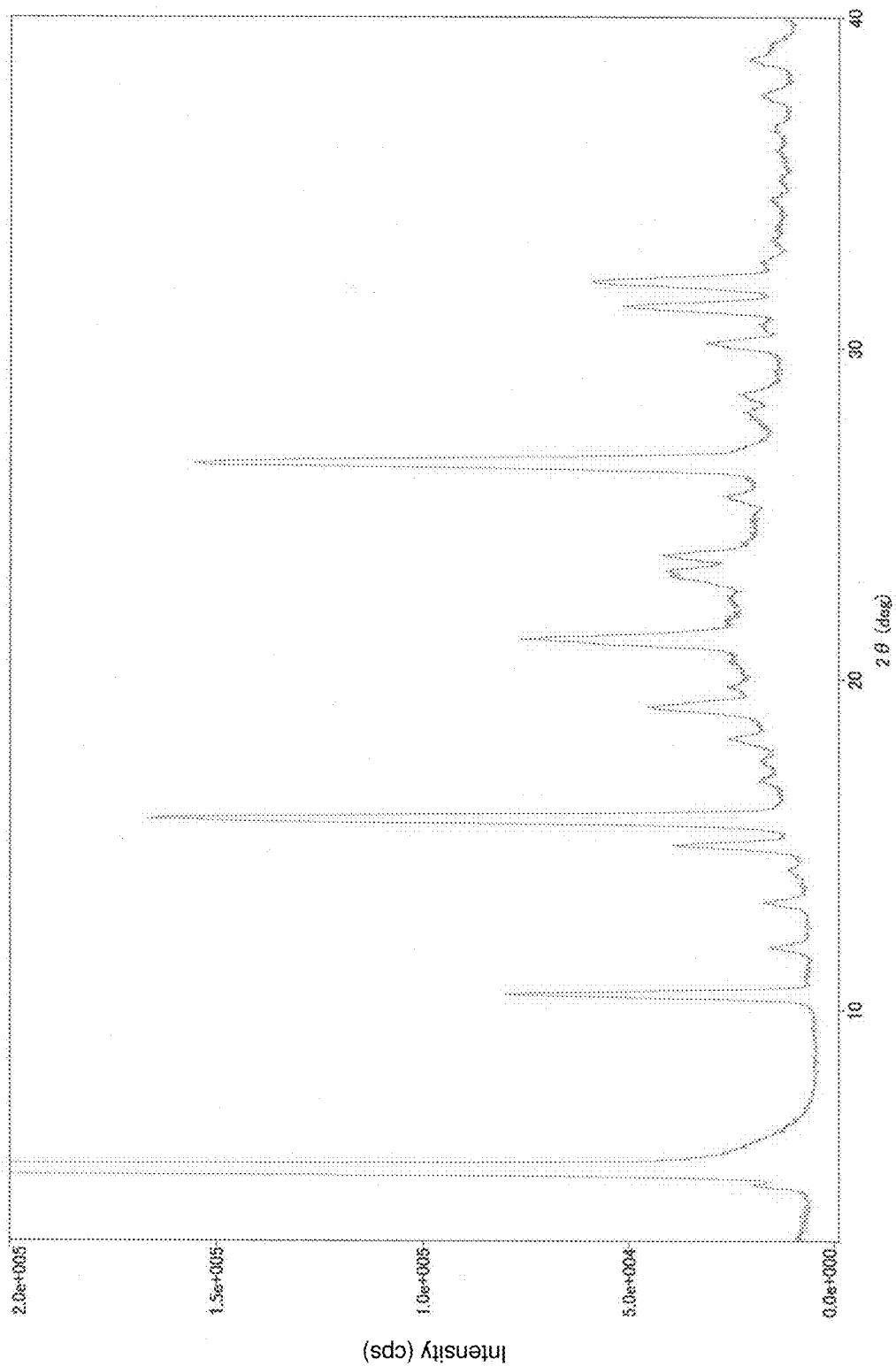

METHOD FOR PRODUCING 1-(ACYLOXY)ALKYL CARBAMATE DERIVATIVE

This application is a national stage application under 35 U.S.C. § 371 of International Application No. PCT/JP2016/068796, filed Jun. 24, 2016, entitled "NOVEL METHOD FOR PRODUCING 1-(ACYLOXY)ALKYL CARBAMATE DERIVATIVE," which claims priority to Japanese Patent Application No. 2015-129196, filed Jun. 26, 2015.

TECHNICAL FIELD

The present invention relates to a novel method for producing a 1-(acyloxy)alkyl carbamate derivative, and a fluorous alkyl carbonate derivative used in the method.

BACKGROUND ART

Prodrug means a pharmaceutical product that is converted to an active ingredient as a result of a reaction with an enzyme, gastric acid, etc., in a living body. Preparation of such a prodrug from a pharmaceutical product is carried out for the purposes of: (1) improving absorbability into a body, (2) reducing side effects, (3) allowing it to act in a specific organ, (4) sustaining the action, and the like.

1-(Acyloxy)alkoxycarbonyl group has been used for conversion of various pharmaceutical molecules having an amino group or the like to prodrugs. A pharmaceutical molecule having an amino group is converted to a prodrug by introducing such a 1-(acyloxy)alkoxycarbonyl group, so that the pharmaceutical molecule is converted to a 1-(acyloxy)alkyl carbamate derivative (Non Patent Literatures 1 and 2).

Patent Literature 1 discloses 1-(acyloxy)alkyl carbamate derivatives (Examples 20, 22, 23, 27, 28, 29, 30, 31, and 32 of Patent Literature 1) as prodrugs of compounds showing TAFIa inhibitory activity (Examples 15 and 40 of Patent Literature 1).

As methods of synthesizing 1-(acyloxy)alkyl carbamate derivatives, the methods disclosed in Patent Literatures 2 to 8, etc. are known. However, these methods have been disadvantageous in that they need multi-stage reaction steps, in that they provide a low yield, in that they generate by-products, which are hardly removed, etc.

CITATION LIST

Patent Literature

Patent Literature 1: International Publication No. WO 2011/115064
Patent Literature 2: U.S. Pat. No. 4,916,230
Patent Literature 3: International Publication No. WO 03/077902
Patent Literature 4: International Publication No. WO 03/104184
Patent Literature 5: International Publication No. WO 2005/010011
Patent Literature 6: International Publication No. WO 2005/066122
Patent Literature 7: International Publication No. WO 2010/017504
Patent Literature 8: U.S. Patent Application Laid-Open No. 2014/0243544

Non Patent Literature

Non Patent Literature 1: Bioorg. Med. Chem. Lett., 7, pp. 1811-1816 (1997)

Non Patent Literature 2: J. Med. Chem., 31, pp. 318-322 (1988)

SUMMARY OF INVENTION

Technical Problem

It is an object of the present invention to provide a method for efficiently and simply producing a 1-(acyloxy)alkyl carbamate derivative.

Solution to Problem

The present inventors have found that a 1-(acyloxy)alkyl carbamate derivative can be produced using a fluorous alkyl carbonate derivative. The inventors have found that fluorous alcohol generated as a by-product can be easily removed by a simple concentration operation, and that a good-quality 1-(acyloxy)alkyl carbamate derivative can be efficiently and simply produced.

Specifically, the present invention includes the following inventions.

(1) A method for producing a compound represented by the following formula (III) or a pharmacologically acceptable salt thereof:

[Formula 3]

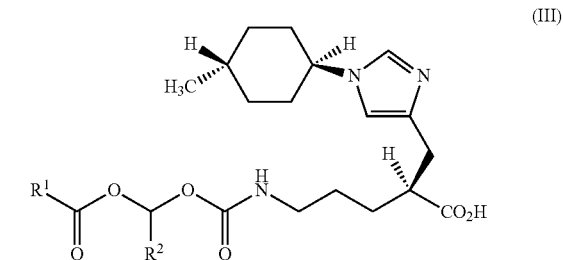

wherein $R^1$ represents a $C_1$-$C_4$ alkyl group or a $C_3$-$C_6$ cycloalkyl group, and $R^2$ represents a $C_1$-$C_4$ alkyl group or a hydrogen atom, wherein the method comprises allowing a compound represented by the following formula (I):

[Formula 1]

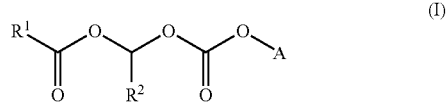

wherein $R^1$ and $R^2$ are the same as defined above, and A represents a fluorous alkyl group (wherein the fluorous alkyl group represents a $C_2$-$C_{11}$ alkyl group in which 40% or more of the hydrogen atoms are replaced by fluorine atoms), to come into contact with a compound represented by the following formula (II) or a salt thereof:

[Formula 2]

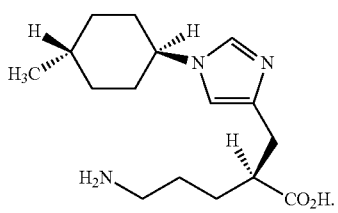
(II)

(2) The production method according to the above (1), wherein the fluorous alkyl group is a 1,1,1,3,3,3-hexafluoro-2-propyl group.

(3) The production method according to the above (1) or (2), wherein $R^1$ is an isopropyl group and $R^2$ is a methyl group.

(4) The production method according to the above (1), which is a method for producing a compound represented by the following formula (VII) or a pharmacologically acceptable salt thereof:

[Formula 6]

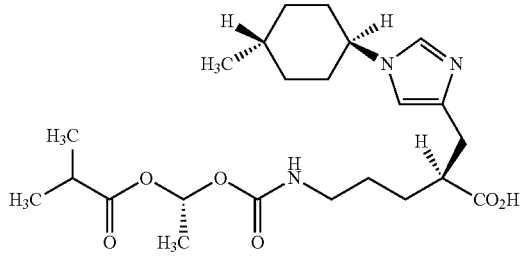
(VII)

wherein the method comprises allowing a compound represented by the following formula (VI):

[Formula 4]

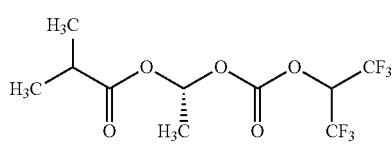
(VI)

to come into contact with a compound represented by the following formula (II) or a salt thereof:

[Formula 5]

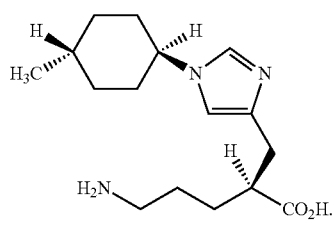
(II)

(5) The production method according to the above (1), which is a method for producing a compound represented by the following formula (IX) or a pharmacologically acceptable salt thereof:

[Formula 9]

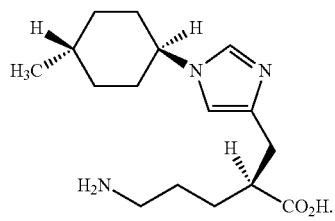
(IX)

wherein the method comprises allowing a compound represented by the following formula (VIII):

[Formula 7]

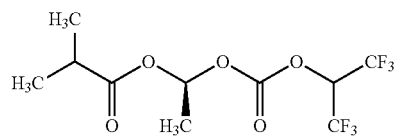
(VIII)

to come into contact with a compound represented by the following formula (II) or a salt thereof:

[Formula 8]

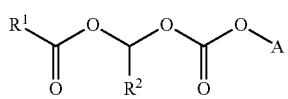
(II)

(6) A compound represented by the following formula (I):

[Formula 10]

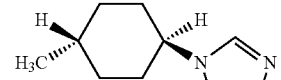
(I)

wherein $R^1$ represents a $C_1$-$C_4$ alkyl group or a $C_3$-$C_6$ cycloalkyl group, $R^2$ represents a $C_1$-$C_4$ alkyl group or a hydrogen atom, and A represents a fluorous alkyl group (wherein the fluorous alkyl group represents a $C_2$-$C_{11}$ alkyl group in which 40% or more of the hydrogen atoms are replaced by fluorine atoms).

(7) The compound according to the above (6), wherein the fluorous alkyl group is a 1,1,1,3,3,3-hexafluoro-2-propyl group.

(8) The compound according to the above (6) or (7), wherein $R^1$ is an isopropyl group and $R^2$ is a methyl group.

(9) The compound according to the above (6), which is represented by the following formula (VI):

[Formula 11]

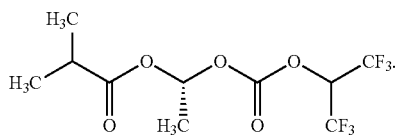

(VI)

(10) The compound according to the above (6), which is represented by the following formula (VIII):

[Formula 12]

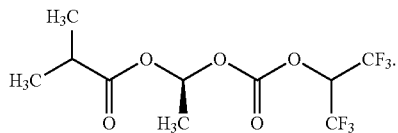

(VIII)

(11) A method for producing a compound represented by the following formula (I):

[Formula 15]

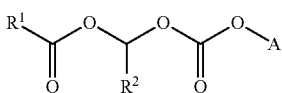

(I)

wherein $R^1$ represents a $C_1$-$C_4$ alkyl group or a $C_3$-$C_6$ cycloalkyl group, $R^2$ represents a $C_1$-$C_4$ alkyl group or a hydrogen atom, and A represents a fluorous alkyl group (wherein the fluorous alkyl group represents a $C_2$-$C_{11}$ alkyl group in which 40% or more of the hydrogen atoms are replaced by fluorine atoms), wherein the method comprises allowing a compound represented by the following formula (IV):

[Formula 13]

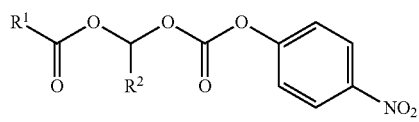

(IV)

wherein $R^1$ and $R^2$ are the same as defined above, to come into contact with a compound represented by the following formula (V):

[Formula 14]

(V)

wherein A is the same as defined above.

(12) The production method according to the above (11), wherein the fluorous alkyl group is a 1,1,1,3,3,3-hexafluoro-2-propyl group.

(13) The production method according to the above (11) or (12), wherein $R^1$ is an isopropyl group and $R^2$ is a methyl group.

(14) A method for producing a compound represented by the following formula (VI):

[Formula 18]

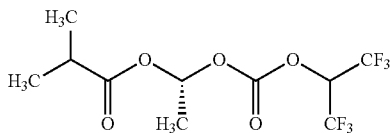

(VI)

wherein the method comprises a step of allowing a compound represented by the following formula (XI):

[Formula 16]

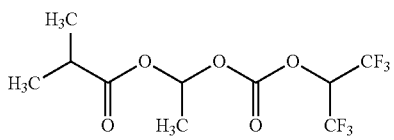

(XI)

to react with an enzyme in an inert solvent to hydrolyze a compound represented by the following formula (VIII):

[Formula 17]

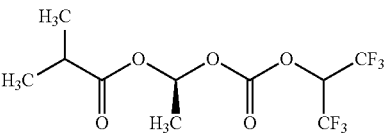

(VIII)

(wherein the enzyme has the property of selectively hydrolyzing the compound represented by the formula (VIII)), and then removing a product obtained by the hydrolysis.

(15) The production method according to the above (14), wherein the enzyme is lipase derived from *Candida antarctica*, lipase derived from *Candida rugosa*, or lipase derived from *Themomyces lanuginosus*.

(16) The production method according to the above (15), wherein the enzyme is lipase derived from *Candida antarctica*.

(17) The production method according to the above (16), wherein the enzyme is CHIRAZYME L-2,C4.

(18) The production method according to any one of the above (14) to (17), wherein the inert solvent is a solvent comprising a buffer.

(19) The production method according to any one of the above (14) to (17), wherein the inert solvent is a solvent comprising a phosphate buffer.

(20) Crystals of a compound represented by the following formula (VII):

[Formula 19]

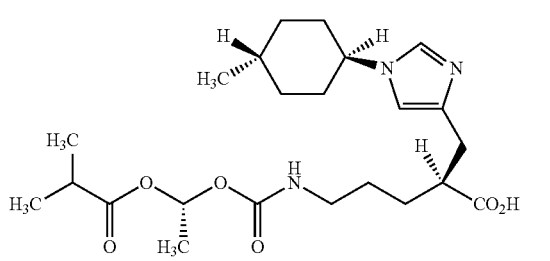

(VII)

wherein the crystals show main peaks at diffraction angles (2θ) of 5.2±0.2°, 10.5±0.2°, 15.8±0.2°, 26.5±0.2°, and 26.6±0.2° in a powder X-ray diffraction obtained by irradiation of the crystals with a copper Kα ray.

(21) A method for producing a compound represented by the following formula (VII) or a pharmacologically acceptable salt thereof:

[Formula 21]

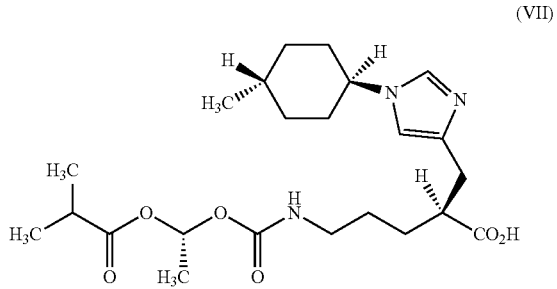

(VII)

wherein the method comprises a step of crystallizing the crystals according to the above (20) from a solution comprising a compound represented by the following formula (X):

[Formula 20]

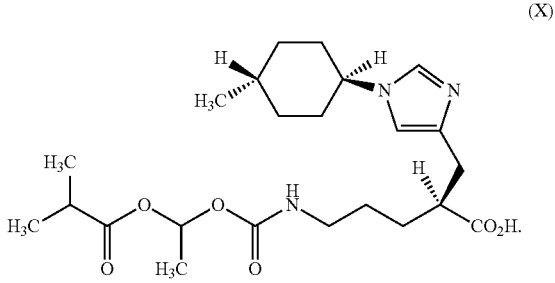

(X)

(22) The production method according to the above (21), wherein the solution is a solution comprising ethyl acetate.

(23) The production method according to the above (21) or (22), wherein the crystallization is carried out under conditions of −5° C. to 5° C.

(24) The production method according to any one of the above (21) to (23), which is carried out following the production method according to the above (3).

Advantageous Effects of Invention

According to the present invention, a method for efficiently and simply producing a good-quality 1-(acyloxy) alkyl carbamate derivative can be provided.

BRIEF DESCRIPTION OF DRAWING

FIG. 1 is a view showing the results of a powder X-ray diffraction obtained by irradiation of crystals of a compound represented by formula (VII) with a copper Kα ray.

DESCRIPTION OF EMBODIMENTS

Hereinafter, the substituents used in the present description will be described.

A "$C_1$-$C_4$ alkyl group" in $R^1$ and $R^2$ means a linear or branched saturated hydrocarbon group having 1 to 4 carbon atoms. Examples thereof include a methyl group, an ethyl group, a propyl group, an isopropyl group, an n-butyl group, a sec-butyl group, and a tert-butyl group.

A "$C_1$-$C_4$ alkyl group" in $R^1$ is preferably a methyl group, an ethyl group, an isopropyl group or a tert-butyl group, more preferably an isopropyl group or a tert-butyl group, and most preferably an isopropyl group.

A "$C_3$-$C_6$ cycloalkyl group" in $R^1$ means a group consisting of a saturated hydrocarbon ring having 3 to 6 carbon atoms. Examples thereof include a cyclopropyl group, a cyclobutyl group, a cyclopentyl group, and a cyclohexyl group.

A "$C_3$-$C_6$ cycloalkyl group" in $R^1$ is preferably a cyclobutyl group, a cyclopentyl group or a cyclohexyl group, more preferably a cyclopentyl group or a cyclohexyl group, and most preferably a cyclohexyl group.

The $R^1$ as a whole is preferably a methyl group, an ethyl group, an isopropyl group, a tert-butyl group or a cyclohexyl group, more preferably an isopropyl group, a tert-butyl group or a cyclohexyl group, and most preferably an isopropyl group.

A "$C_1$-$C_4$ alkyl group" in $R^2$ is preferably a methyl group, an ethyl group or an isopropyl group, more preferably a methyl group or an ethyl group, and most preferably a methyl group.

The $R^2$ as a whole is preferably a hydrogen atom, a methyl group, an ethyl group or an isopropyl group, more preferably a hydrogen atom, a methyl group or an ethyl group, and most preferably a methyl group.

A "fluorous alkyl group" in A means a $C_2$-$C_{11}$ alkyl group, in which 40% or more of the hydrogen atoms are replaced by fluorine atoms. Examples thereof include a 2,2-difluoroethyl group, a 2,2,2-trifluoroethyl group, a 2,2,3,3,3-pentafluoro-1-propyl group, a 1,1,1,3,3,3-hexafluoro-2-propyl group, a 2,2,3,4,4,4-hexafluoro-1-butyl group, a 2,2,3,3,4,4,4-heptafluoro-1-butyl group, a nonafluoro-tert-butyl group, a 2,2,3,3,4,4,5,5-octafluoro-1-pentyl group, a 1H,1H-nonafluoro-1-pentyl group, a 1H,1H,2H,2H-nonafluoro-1-hexyl group, a 1H,1H,7H-dodecafluoro-1-heptyl group, a 1H,1H-tridecafluoro-1-heptyl group, a 1H,1H,2H,2H-tridecafluoro-1-n-octyl group, a 1H,1H-pentadecafluoro-1-octyl group, a 1H, 1H, 9H-hexadecafluoro-1-nonanyl group, a 1H,1H-heptadecafluoro-1-nonanyl group, a 1H,1H,2H,2H-heptadecafluoro-1-decanyl group, a 1H,1H-nonadecafluoro-1-decanyl group, and a 1H,1H,11H-eicosafluoro-1-undecanyl group.

Such a "fluorous alkyl group" in A is preferably a 2,2,2-trifluoroethyl group, a 2,2,3,3,3-pentafluoro-1-propyl group, a 1,1,1,3,3,3-hexafluoro-2-propyl group, a 2,2,3,4,4,4- hexafluoro-1-butyl group, a 2,2,3,3,4,4,4-heptafluoro-1-butyl group or a nonafluoro-tert-butyl group, more preferably a 2,2,2-trifluoroethyl group, a 2,2,3,3,3-pentafluoro-1-propyl group, a 1,1,1,3,3,3-hexafluoro-2-propyl group, a 2,2,3,4,4,4-hexafluoro-1-butyl group or a 2,2,3,3,4,4,4-heptafluoro-1-butyl group, and most preferably a 1,1,1,3,3,3-hexafluoro-2-propyl group.

The production method of the present invention can be carried out as follows.

[Formula 22]

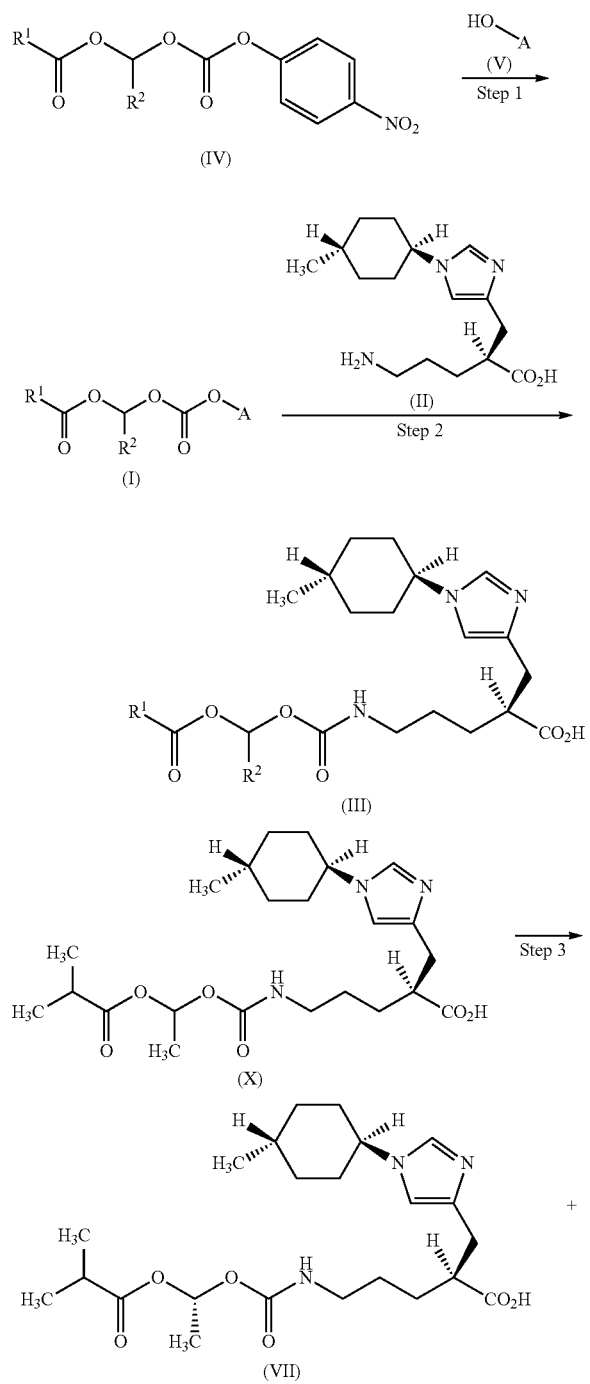

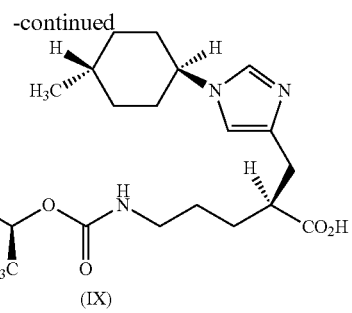

Step 1:

The present step is a step of allowing a compound represented by the formula (IV) [wherein $R^1$ represents a $C_1$-$C_4$ alkyl group or a $C_3$-$C_6$ cycloalkyl group, and $R^2$ represents a $C_1$-$C_4$ alkyl group or a hydrogen atom] to come into contact with a compound represented by the formula (V) [wherein A represents a fluorous alkyl group (wherein the fluorous alkyl group represents a $C_2$-$C_{11}$ alkyl group in which 40% or more of the hydrogen atoms are replaced by fluorine atoms)] to produce a compound represented by the formula (I) [wherein $R^1$, $R^2$ and A are the same as defined above] (i.e., a fluorous alkyl carbonate derivative).

The compound represented by the formula (IV) can be produced by the method described in Bioorg. Med. Chem. Lett., 7, pp. 1811-1816 (1997) or J. Med. Chem., 31, pp. 318-322 (1988), or a method equivalent thereto.

The compound represented by the formula (V) is fluorous alcohol, and a commercially available product can be used. Examples thereof include 2,2-difluoroethanol, 2,2,2-trifluoroethanol, 2,2,3,3,3-pentafluoro-1-propanol, 1,1,1,3,3,3-hexafluoro-2-propanol, 2,2,3,4,4,4-hexafluoro-1-butanol, 2,2,3,3,4,4,4-heptafluoro-1-butanol, nonafluoro-tert-butanol, 2,2,3,3,4,4,5,5-octafluoro-1-pentanol, 1H,1H-nonafluoro-1-pentanol, 1H,1H,2H,2H-nonafluoro-1-hexanol, 1H,1H,7H-dodecafluoro-1-heptanol, 1H,1H-tridecafluoro-1-heptanol, 1H,1H,2H,2H-tridecafluoro-1-n-octanol, 1H,1H-pentadecafluoro-1-octanol, 1H, 1H, 9H-hexadecafluoro-1-nonanol, 1H,1H-heptadecafluoro-1-nonanol, 1H,1H,2H,2H-heptadecafluoro-1-decanol, 1H,1H-nonadecafluoro-1-decanol, and 1H,1H,11H-eicosafluoro-1-undecanol. The compound represented by the formula (V) is preferably 2,2,2-trifluoroethanol, 2,2,3,3,3-pentafluoro-1-propanol, 1,1,1,3,3,3-hexafluoro-2-propanol, 2,2,3,4,4,4-hexafluoro-1-butanol, 2,2,3,3,4,4,4-heptafluoro-1-butanol or nonafluoro-tert-butanol, more preferably 2,2,2-trifluoroethanol, 2,2,3,3,3-pentafluoro-1-propanol, 1,1,1,3,3,3-hexafluoro-2-propanol, 2,2,3,4,4,4-hexafluoro-1-butanol or 2,2,3,3,4,4,4-heptafluoro-1-butanol, and most preferably 1,1,1,3,3,3-hexafluoro-2-propanol.

The solvent used in the present step is not particularly limited, as long as it does not inhibit the reaction. Examples thereof include acetonitrile, dichloromethane, chloroform, methanol, ethanol, diethyl ether, 1,2-dimethoxyethane, tetrahydrofuran, 1,4-dioxane, ethyl acetate, hexane, pentane, benzene, toluene, chlorobenzene, acetone, 2-butanone, N,N-dimethylformamide, N,N-dimethylacetamide, 1-methyl-2-pyrrolidone, dimethyl sulfoxide, water, and a mixed solvent thereof. The solvent used herein is preferably acetonitrile.

The compound represented by the formula (V) is used in the present step in an amount of generally 1 to 10 equivalents, and preferably 1.5 to 4 equivalents, based on the amount of the compound represented by the formula (IV).

A base is preferably used in the present step. Examples of the base include triethylamine, tributylamine, diisopropylethylamine, N-methylmorpholine, N-methylpyrrolidine, N-methylpiperidine, pyridine, 2-methylpyridine, 2,6-dimethylpyridine, 4-dimethylaminopyridine, 1,4-diazabicyclo[2.2.2]octane, 1,8-diazabicyclo[5.4.0]undec-7-ene, and 1,5-diazabicyclo[4.3.0]undec-7-ene. The base used herein is preferably triethylamine. The base is used in an amount of generally 1 to 10 equivalents, and preferably 1 to 1.2 equivalents, based on the amount of the compound represented by the formula (IV).

The reaction temperature applied in the present step is generally −40° C. to 80° C., and preferably −10° C. to 15° C.

The reaction time applied in the present step is generally 1 hour to 72 hours, and preferably 2 hours to 6 hours.

Step 2:

The present step is a step of allowing the compound represented by the formula (I) [wherein $R^1$ represents a $C_1$-$C_4$ alkyl group or a $C_3$-$C_6$ cycloalkyl group, $R^2$ represents a $C_1$-$C_4$ alkyl group or a hydrogen atom, and A represents a fluorous alkyl group (wherein the fluorous alkyl group represents a $C_2$-$C_{11}$ alkyl group in which 40% or more of the hydrogen atoms are replaced by fluorine atoms)] (i.e., a fluorous alkyl carbonate derivative) to come into contact with a compound represented by the formula (II) or a salt thereof, to produce a compound represented by the formula (III) [wherein $R^1$ and $R^2$ are the same as defined above] (i.e., a 1-(acyloxy)alkyl carbamate derivative) or a pharmacologically acceptable salt thereof.

According to the present step, fluorous alcohol corresponding to A in the compound represented by the formula (I) is generated as a by-product. Examples of such a compound include 2,2-difluoroethanol, 2,2,2-trifluoroethanol, 2,2,3,3,3-pentafluoro-1-propanol, 1,1,1,3,3,3-hexafluoro-2-propanol, 2,2,3,4,4,4-hexafluoro-1-butanol, 2,2,3,3,4,4,4-heptafluoro-1-butanol, nonafluoro-tert-butanol, 2,2,3,3,4,4,5,5-octafluoro-1-pentanol, 1H,1H-nonafluoro-1-pentanol, 1H,1H,2H,2H-nonafluoro-1-hexanol, 1H,1H,7H-dodecafluoro-1-heptanol, 1H,1H-tridecafluoro-1-heptanol, 1H,1H,2H,2H-tridecafluoro-1-n-octanol, 1H,1H-pentadecafluoro-1-octanol, 1H,1H,9H-hexadecafluoro-1-nonanol, 1H,1H-heptadecafluoro-1-nonanol, 1H,1H,2H,2H-heptadecafluoro-1-decanol, 1H,1H-nonadecafluoro-1-decanol, and 1H,1H,11H-eicosafluoro-1-undecanol. Since, in particular, fluorous alcohol having a $C_2$-$C_6$ alkyl group is a compound having a low boiling point, it can be easily removed by a simple concentration operation.

The compound represented by the formula (II) or a salt thereof can be produced by the method described in International Publication No. WO 2011/115064 or a method equivalent thereto (the compound represented by the formula (II) is described in Example 15, and a p-toluenesulfonate-anhydride of this compound is described in Example 40).

The solvent used in the present step is not particularly limited, as long as it does not inhibit the reaction. Examples thereof include acetonitrile, dichloromethane, chloroform, methanol, ethanol, diethyl ether, 1,2-dimethoxyethane, tetrahydrofuran, 1,4-dioxane, ethyl acetate, hexane, pentane, benzene, toluene, chlorobenzene, acetone, 2-butanone, N,N-dimethylformamide, N,N-dimethylacetamide, 1-methyl-2-pyrrolidone, dimethyl sulfoxide, water, and a mixed solvent thereof. The solvent used herein is preferably acetonitrile.

The compound represented by the formula (I) is used in the present step in an amount of generally 1 to 15 equivalents, and preferably 1 to 1.5 equivalents, based on the amount of the compound represented by the formula (II).

A base is preferably used in the present step. Examples of the base include triethylamine, tributylamine, diisopropylethylamine, N-methylmorpholine, N-methylpyrrolidine, N-methylpiperidine, pyridine, 2-methylpyridine, 2,6-dimethylpyridine, 4-dimethylaminopyridine, 1,4-diazabicyclo[2.2.2]octane, 1,8-diazabicyclo[5.4.0]undec-7-ene, and 1,5-diazabicyclo[4.3.0]non-7-ene. The base used herein is preferably triethylamine. The base is used in an amount of generally 1 to 10 equivalents, and preferably 1 to 2 equivalents, based on the amount of the compound represented by the formula (II).

When the compound represented by the formula (II) is an acid-addition salt formed with an acid (wherein examples of the acid-addition salt include: hydrohalides such as hydrofluoride, hydrochloride, hydrobromide, and hydroiodide; inorganic acid salts such as nitrate, perchlorate, sulfate, and phosphate; lower alkanesulfonates such as methanesulfonate, trifluoromethanesulfonate, and ethanesulfonate; arylsulfonates such as benzenesulfonate and p-toluenesulfonate; organic acid salts such as acetate, malate, fumarate, succinate, citrate, tartrate, oxalate, and maleate; and amino acid salts such as ornitate, glutamate, and aspartate, and a preferred example is p-toluenesulfonate), an additional base other than the above described bases is preferably used. Examples of such an additional base include sodium hydroxide, potassium hydroxide, lithium hydroxide, calcium hydroxide, barium hydroxide, sodium carbonate, potassium carbonate, sodium hydrogen carbonate, potassium hydrogen carbonate, aqueous solutions thereof, and 1,8-diazabicyclo[5.4.0]undec-7-ene. Preferred examples include an aqueous solution of sodium hydroxide and 1,8-diazabicyclo[5.4.0]undec-7-ene. The base is used in an amount of generally 1 to 10 equivalents, and preferably 1 to 1.1 equivalents, based on the amount of the compound represented by the formula (II).

The reaction temperature applied in the present step is generally −80° C. to 40° C., and preferably −40° C. to 20° C.

The reaction time applied in the present step is generally 1 hour to 72 hours, and preferably 2 hours to 30 hours.

Step 3:

The present step is a step of crystallizing crystals of a compound represented by the formula (VII) from a solution comprising a compound represented by the formula (X) (which corresponds to the compound represented by the formula (III), in which $R^1$ is an isopropyl group and $R^2$ is a methyl group) to produce a compound represented by the formula (VII) or a pharmacologically acceptable salt thereof. The crystals of the compound represented by the formula (VII) are characterized in that they show main peaks at diffraction angles (2θ) of 5.2°, 10.5°, 15.8°, 26.5°, and 26.6° in a powder X-ray diffraction obtained by irradiation of the crystals with a copper Kα ray. In general, the diffraction angle (2θ) used in the powder X-ray diffraction may have an error in the range of ±0.2°, it being understood that the value of the above described diffraction angle also includes numerical values in the aforementioned range. Accordingly, not only the crystals completely identical to the above described diffraction angles, but also crystals having main peaks at diffraction angles (2θ) of 5.2±0.2°, 10.5±0.2°, 15.8±0.2°, 26.5±0.2°, and 26.6±0.2°, are considered to be the present crystals, and thus, these crystals are also included in the present invention. In the present invention, "±0.2°" means a numerical value in the range of +0.2° to −0.2° with respect to a specific numerical value. For example, "5.2±0.2°" means a numerical value in the range of 5.0° to 5.4°.

The solvent used in the present step is not particularly limited, as long as it does not inhibit crystallization of crystals of the compound represented by the formula (VII). The solvent is preferably an ethyl acetate solution. The crystals of the compound represented by the formula (VII) can be crystallized preferably under conditions of −20° C. to 30° C., and more preferably under conditions of −5° C. to 5° C.

It is to be noted that the present step can also be carried out by separating the compound represented by the formula (X) into a compound represented by the formula (VII) and a compound represented by the formula (IX), using optically active column chromatography.

Alternatively, the production method of the present invention can also be carried out as follows.

[Formula 23]

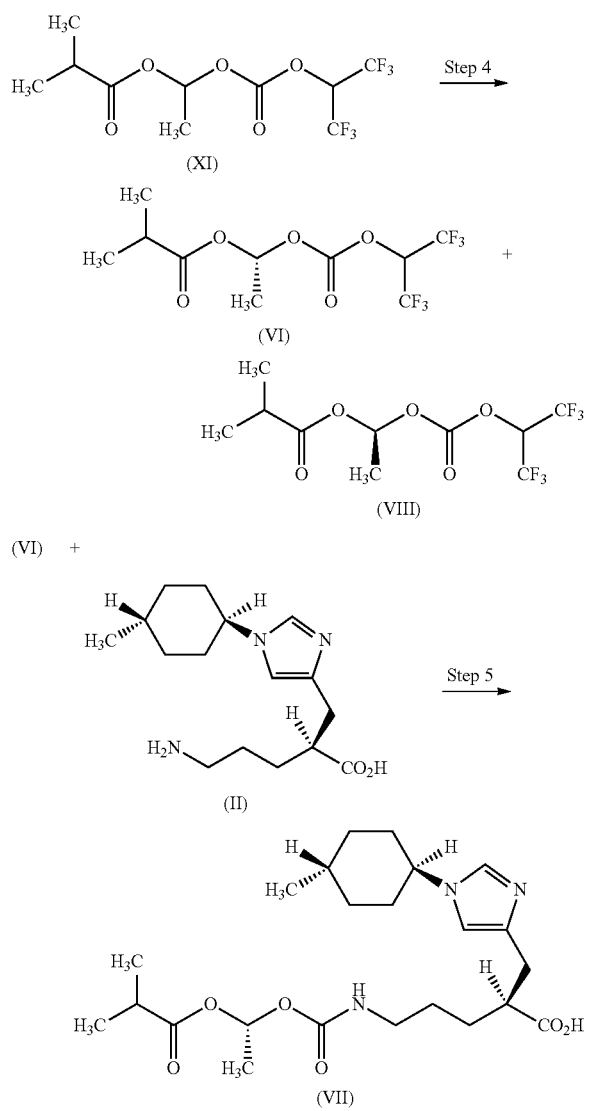

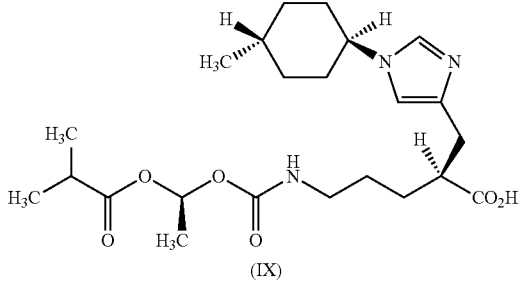

Step 4:

The present step is a step of subjecting a compound represented by the formula (XI) to optical resolution to obtain a compound represented by the formula (VI) and a compound represented by the formula (VIII). Optical resolution can be carried out using optically active column chromatography.

Moreover, the compound represented by the formula (VI) can be obtained by performing optical resolution using an enzyme. Such optical resolution using an enzyme can be carried out by allowing the compound represented by the formula (XI) to react with an enzyme that selectively hydrolyzes the compound represented by the formula (VIII) in an inert solvent. The inert solvent used in the present step is not particularly limited, as long as it does not inhibit the reaction. The inert solvent is preferably a mixed solvent of a buffer and an organic solvent. Examples of the buffer include an acetate buffer, a phosphate buffer, a citrate buffer, a borate buffer, a tartrate buffer, and a Tris buffer. The inert solvent used herein is preferably a phosphate buffer. Examples of the organic solvent include: nitrile solvents such as acetonitrile; ether solvents such as diethyl ether, 1,2-dimethoxyethane, and tetrahydrofuran; saturated hydrocarbon solvents such as hexane and pentane; aromatic hydrocarbon solvents such as benzene, toluene, and chlorobenzene; ketone solvents such as acetone and 2-butanone; amide solvents such as N,N-dimethylformamide, N,N-dimethylacetamide, and 1-methyl-2-pyrrolidone; alcohol solvents such as methanol and ethanol; and sulfoxide solvents such as dimethyl sulfoxide. The organic solvent is preferably dimethyl sulfoxide.

The enzyme used in the present step is not particularly limited, as long as it is an enzyme that selectively hydrolyzes the compound represented by the formula (VIII). Preferred examples of the enzyme include lipase derived from *Candida antarctica* (e.g., CHIRAZYME L-2,C3, CHIRAZYME L-2,C4, CHIRAZYME L-2,CA, and CHIRAZYME L-2, CB), lipase derived from *Candida rugosa* (e.g., lipase AY "Amano" 30), and lipase derived from *Themomyces lanuginosus* (e.g., CHIRAZYME L-8.1). The enzyme used herein is more preferably lipase derived from *Candida antarctica*, and even more preferably CHIRAZYME L-2,C4. The enzyme is used in the present step in an amount of generally 1/100 to 10 times, more preferably 1/50 to 1 time, and even more preferably 1/20 to 1/5 times greater than the mass of a mixture of the compound (1) and the compound (2).

The reaction temperature applied in the present step is generally 0° C. to 80° C., preferably 10° C. to 65° C., and more preferably 10° C. to 30° C.

The reaction time applied in the present step is generally 1 hour to 120 hours, preferably 5 hours to 80 hours, and more preferably 10 hours to 60 hours.

Step 5:

The present step is a step of allowing the compound represented by formula (VI) to come into contact with the compound represented by the formula (II) or a salt thereof to produce a compound represented by the formula (VII) or a pharmacologically acceptable salt thereof. The present step can be carried out by the same method as that in the step 2.

Step 6:

The present step is a step of allowing the compound represented by formula (VIII) to come into contact with the compound represented by the formula (II) or a salt thereof to produce a compound represented by the formula (IX) or a pharmacologically acceptable salt thereof. The present step can be carried out by the same method as that in the step 2.

The compounds represented by the formula (III), the formula (VII) and the formula (IX) can be converted to pharmacologically acceptable salts by allowing the compounds to react with an acid or a base existing in the reaction system, or by adding a suitable acid or base into the reaction system, as necessary, and then allowing the compounds to react with it.

Regarding the pharmacologically acceptable salts of the compounds represented by the formula (III), the formula (VII) and the formula (IX), examples of acid-addition salts formed with acids can include: hydrohalides such as hydrofluoride, hydrochloride, hydrobromide, and hydroiodide; inorganic acid salts such as nitrate, perchlorate, sulfate, and phosphate; lower alkanesulfonates such as methanesulfonate, trifluoromethanesulfonate, and ethanesulfonate; arylsulfonates such as benzenesulfonate and p-toluenesulfonate; organic acid salts such as acetate, malate, fumarate, succinate, citrate, tartrate, oxalate, and maleate; and amino acid salts such as ornitate, glutamate, and aspartate.

In addition, examples of base-addition salts formed with bases can include: alkali metal salts such as sodium salts, potassium salts, and lithium salts; alkaline-earth metal salts such as calcium salts and magnesium salts; inorganic salts such as ammonium salts; organic amine salts such as dibenzylamine salts, morpholine salts, phenylglycine alkyl ester salts, ethylenediamine salts, N-methylglucamine salts, diethylamine salts, triethylamine salts, cyclohexylamine salts, dicyclohexylamine salts, N,N'-dibenzylethylenediamine salts, diethanolamine salts, N-benzyl-N-(2-phenylethoxy)amine salts, piperazine salts, tetramethylammonium salts, and tris(hydroxymethyl)aminomethane salts; and amino acid salts such as arginine salts.

Furthermore, the compound represented by the formula (III) or a pharmacologically acceptable salt thereof may also be present in the form of a solvate, and such a solvate is also included in the compound represented by the formula (III) or a pharmacologically acceptable salt thereof. The solvate is not particularly limited, as long as it is a pharmacologically acceptable solvate. Specifically, the solvate is preferably a hydrate, an ethanol solvate, etc., and is more preferably a hydrate.

After completion of the reaction, the products generated in the above described step 1 to step 6 can be isolated from the reaction mixture, as necessary, according to a conventional method, for example, (1) a method of directly concentrating the reaction solution, (2) a method comprising removing insoluble matters from the reaction mixture by filtration, and then concentrating the filtrate, (3) a method comprising adding water and a solvent immiscible with water (e.g., dichloromethane, diethyl ether, ethyl acetate, toluene, etc.) to the reaction solution, and then extracting a product, or (4) a method of collecting a crystallized or precipitated product by filtration. The thus isolated product can be purified, as necessary, according to a conventional method, for example, vacuum distillation, atmospheric distillation, recrystallization, reprecipitation, or various types of chromatography. Otherwise, the product generated in each step can be used in the subsequent step without isolation or purification.

The compounds represented by the formula (III), the formula (VII) and the formula (IX) obtained by the method of the present invention are useful as prodrugs of TAFIa inhibitors. Accordingly, the compounds represented by the formula (III), the formula (VII) and the formula (IX) can be used as therapeutic agents for myocardial infarction, angina pectoris, acute coronary syndrome, cerebral infarction, deep vein thrombosis, pulmonary embolism, peripheral arterial embolism, sepsis, disseminated intravascular coagulation syndrome, pulmonary fibrosis, etc.

It is to be noted that the compound represented by the formula (I) (i.e., a fluorous alkyl carbonate derivative) can also be used for the purpose of producing 1-(acyloxy)alkyl carbamate derivatives other than the compounds represented by the formula (III), the formula (VII) and the formula (IX).

EXAMPLES

Hereinafter, the present invention will be specifically described in the following examples. However, these examples are not intended to limit the scope of the present invention.

The symbol "$^1$H-NMR" in the Examples means a "nuclear magnetic resonance spectrum". The $CDCl_3$ inside the parentheses means deuterated chloroform that is a measurement solvent. As an internal standard, TMS (tetramethylsilane) was used. Multiplicity in $^1$H-NMR means s=singlet, d=doublet, t=triplet, q=quartet, hept=heptet, m=multiplet, and brs=broad singlet.

[Example 1] 1-{[(1,1,1,3,3,3-Hexafluoro-2-propoxy)carbonyl]oxy}ethyl isobutyrate

[Formula 24]

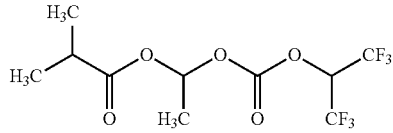

(Method 1)

A solution of 1-{[(4-nitrophenoxy)carbonyl]oxy}ethyl isobutyrate (Bioorg. Med. Chem. Lett., 7, pp. 1811-1816 (1997)) (7.0 g, 23.54 mmol) and 1,1,1,3,3,3-hexafluoro-2-propanol (11.87 g, 70.65 mmol) in acetonitrile (35 mL) solution was cooled to 0° C.-5° C., and triethylamine (3.42 mL, 24.72 mmol) was then added dropwise to the reaction solution. The mixed solution was stirred at the same temperature for 4 hours. After confirming the completion of the reaction, methyl tert-butyl ether (70 mL) and water (70 mL) were added to the reaction solution, and the obtained mixture was then stirred, followed by liquid separation. The organic layer was washed with water (70 mL), 10% saline (70 mL), and 3% sodium hydrogen carbonate 10% saline (70 mL). Thereafter, the organic layer was further washed with 3% sodium hydrogen carbonate 10% saline (70 mL) three times, and nitrophenol was removed. The organic layer was washed with 20% saline (70 mL), and was then concentrated under reduced pressure to approximately 10 mL. The obtained residue was subjected to purification through distillation (degree of vacuum: 1 kPa, a fraction of 75° C.-80° C. was fractionated), so as to obtain the title compound in the form of an oily substance (6.02 g, yield: 78.1%).

$^1$H-NMR (CDCl$_3$) δ: 6.82 (1H, q, J=5.5 Hz), 5.55 (1H, hept, J=5.5 Hz), 2.58 (1H, hept, J=7.0 Hz), 1.58 (3H, d, J=5.5 Hz), 1.18 (6H, d, J=7.0 Hz).

(Method 2)

A solution of 1-{[(4-nitrophenoxy)carbonyl]oxy}ethyl isobutyrate (230 g, 774 mmol) and 1,1,1,3,3,3-hexafluoro-2-propanol (260 g, 1547 mmol) in acetonitrile (1150 mL) was cooled to 0° C.-5° C., and triethylamine (82.23 g, 812 mmol) was then added dropwise to the reaction solution. The mixed solution was stirred at the same temperature for 4 hours. After confirming the completion of the reaction, methyl tert-butyl ether (1150 mL) and n-hexane (1150 mL) at 0° C.-5° C. were added to the reaction solution, and cold water (2300 mL) was also added thereto. The obtained mixture was stirred and was then subjected to liquid separation. The organic layer was washed with cold water (2300 mL) four times, and was then concentrated under reduced pressure to approximately 345 mL. The obtained residue was subjected to purification through distillation (degree of vacuum: 1.5 kPa, a fraction of 70° C.-82° C. was fractionated), so as to obtain the title compound in the form of an oily substance (222.51 g, yield: 88.2%).

[Example 2] (2S)-5-({[1-(Isobutyryloxy)ethoxy]carbonyl}amino)-2-{[1-(trans-4-methylcyclohexyl)-1H-imidazol-4-yl]methyl}valeric acid

[Formula 25]

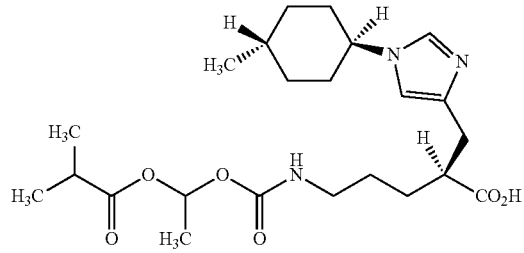

A suspension of (2S)-5-amino-2-{[1-(trans-4-methylcyclohexyl)-1H-imidazol-4-yl]methyl}valeric acid-p-toluenesulfonate-anhydride (2.0 g, 4.30 mmol) in acetonitrile (20 mL) was cooled to −20° C. Thereafter, a 25% aqueous solution of sodium hydroxide (0.69 g, 4.30 mmol), triethylamine (1.19 mL, 8.60 mmol) and the 1-{[(1,1,1,3,3,3-hexafluoro-2-propoxy)carbonyl]oxy}ethyl isobutyrate (1.68 g, 5.15 mmol) obtained in Example 1 were added to the reaction solution, and the obtained mixture was then stirred at −20° C. for 20 hours. Thereafter, concentrated hydrochloric acid (0.36 mL, 4.30 mmol) and ethyl acetate (30 mL) were added to the reaction solution, and 10% saline (20 mL) comprising concentrated hydrochloric acid (0.36 mL, 4.30 mmol) was then poured into the reaction solution. After completion of stirring, the aqueous layer was adjusted to pH 7.0 with concentrated hydrochloric acid, followed by liquid separation, and the organic layer was washed with 20% saline (20 mL) four times. The obtained organic layer was concentrated under reduced pressure to 14 mL, ethyl acetate (40 mL) was then added thereto, and the obtained mixture was then concentrated under reduced pressure to 14 mL. Ethyl acetate (40 mL) was added to the residue, and the obtained mixture was then concentrated under reduced pressure to 14 mL. Heptane (56 mL) was added dropwise to the reaction mixture, and the thus obtained mixture was then stirred at room temperature for 3 hours. Thereafter, the precipitated crystals were filtrated, and the crystals were then washed with heptane (6 mL), followed by vacuum drying, to obtain the title compound in the form of crystals (1.50 g, yield: 77.3%).

$^1$H-NMR (CDCl$_3$) δ: 7.60 (1H, d, J=1.0 Hz), 6.78 (1H, q, J=5.5 Hz), 6.74 (1H, s), 5.03 (1H, brs), 3.87-3.79 (1H, m), 3.22-3.10 (2H, m), 2.88 (1H, dd, J=15.0, 8.5 Hz), 2.78 (1H, dt, J=15.0, 3.5 Hz), 2.70-2.64 (1H, m), 2.53 (1H, tt, J=7.0, 7.0 Hz), 2.14-2.07 (2H, m), 1.90-1.84 (2H, m), 1.78-1.57 (5H, m), 1.49-1.41 (2H, m), 1.44 (1H, t, J=5.5 Hz), 1.15 (6H, d, J=7.0 Hz), 1.15-1.05 (2H, m), 0.96 (3H, d, J=6.5 Hz).

[Example 3] (2S)-5-({[(1R)-1-(Isobutyryloxy)ethoxy]carbonyl}amino)-2-{[1-(trans-4-methylcyclohexyl)-1H-imidazol-4-yl]methyl}valeric acid

[Formula 26]

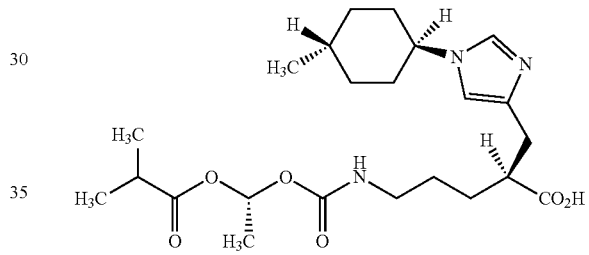

A suspension of (2S)-5-amino-2-{[1-(trans-4-methylcyclohexyl)-1H-imidazol-4-yl]methyl}valeric acid-p-toluenesulfonate-anhydride (1500 g, 3.22 mol) in acetonitrile (13.5 L) was cooled to −5° C. Thereafter, 1,8-diazabicyclo[5.4.0]undec-7-ene (490 g, 3.22 mol), triethylamine (652 g, 6.44 mol) and 1-{[(1,1,1,3,3,3-hexafluoro-2-propoxy)carbonyl]oxy}ethyl isobutyrate (1261 g, 3.87 mol) were added to the reaction solution, and the obtained mixture was then stirred at 0° C. for 4 hours. Thereafter, concentrated hydrochloric acid (326 g, 3.22 mol) and ethyl acetate (13.5 L) were added to the reaction solution, and 20% saline (9 L) comprising concentrated hydrochloric acid (326 g, 3.22 mol) was then poured into the reaction solution. After completion of stirring, the aqueous layer was adjusted to pH 6.4 with concentrated hydrochloric acid, followed by liquid separation, and the organic layer was washed with 20% saline (9 L) five times. To the obtained organic layer, 20% saline (9 L) was added, and after completion of the stirring of the mixture, the aqueous layer was adjusted to pH 6.2 with concentrated hydrochloric acid, followed by liquid separation. The obtained organic layer was concentrated under reduced pressure to 6 L, ethyl acetate (18 L) was then added thereto, and the obtained mixture was then concentrated under reduced pressure to 6 L. Ethyl acetate (6 L) was added to the residue, and the obtained mixture was then concentrated under reduced pressure to 6 L. Ethyl acetate (6 L) was added dropwise to the reaction mixture, and the thus obtained mixture was cooled to 0° C. and was then stirred for 1 hour. Thereafter, the precipitated crystals were filtrated, and the crystals were then washed with cold ethyl acetate (2.3 L), followed by vacuum drying, to obtain crude crystals in the form of white crystals (606 g, yield: 41.6%). The obtained crude crystals (500 g, 1.11 mol) were added to tetrahydrofuran (12.5 L), and the obtained mixture was then stirred at 43° C. Insoluble matters were removed by filtration, and were then washed with tetrahydrofuran (2.5 L). The obtained filtrate was concentrated under reduced pressure to 5 L, ethyl acetate (7.5 L) was then added thereto, and the obtained mixture was then concentrated under reduced pressure to 5 L. Ethyl acetate (7.5 L) was added to the residue, and the obtained mixture was concentrated under reduced pressure again to 5 L, and was then cooled to 0° C., followed by stirring for 1 hour. Thereafter, the precipitated crystals were filtrated, and the crystals were then washed with cold ethyl acetate (1 L), followed by vacuum drying, to obtain the title compound in the form of white crystals (467 g, yield from crude crystals: 93.3%). The absolute configuration of the title compound was confirmed by X-ray crystallography.

$^1$H-NMR (CDCl$_3$) δ: 7.58 (1H, d, J=1.5 Hz), 6.78 (1H, q, J=5.5 Hz), 6.74 (1H, s), 4.98 (1H, t, J=5.5 Hz), 3.84 (1H, tt, J=12.0, 4.0 Hz), 3.22-3.11 (2H, m), 2.86 (1H, dd, J=15.0, 8.5 Hz), 2.78 (1H, dt, J=15.0, 3.0 Hz), 2.70-2.64 (1H, m), 2.52 (1H, tt, J=7.0, 7.0 Hz), 2.14-2.07 (2H, m), 1.90-1.84 (2H, m), 1.78-1.57 (5H, m), 1.49-1.41 (2H, m), 1.44 (1H, d, J=7.0 Hz), 1.15 (6H, dd, J=6.5, 0.5 Hz), 1.15-1.05 (2H, m), 0.95 (3H, d, J=6.5 Hz).

Elemental analysis: based on $C_{23}H_{37}N_3O_6$

Theoretical value: C, 61.18; H, 8.26; N, 9.31; O, 21.26

Measured value: C, 60.92; H, 8.16; N, 9.35; O, 21.29

Powder X-Ray Diffraction:

Powder X-ray diffraction involving irradiation with a copper Kα ray was performed on crystals of the title compound. The results are shown in Table 1 and FIG. 1. Main peaks were observed at diffraction angles (2θ) of 5.2°, 10.5°, 15.8°, 26.5°, and 26.6°.

TABLE 1

| Diffraction angle 2θ (°) | Spacing d (Å) | Relative intensity (%) |
| --- | --- | --- |
| 5.2 | 16.7 | 100.0 |
| 10.5 | 8.5 | 3.9 |
| 10.6 | 8.4 | 0.8 |
| 11.9 | 7.5 | 0.5 |
| 13.3 | 6.7 | 0.6 |
| 14.2 | 6.2 | 0.1 |
| 15.0 | 5.9 | 1.6 |
| 15.7 | 5.7 | 2.6 |
| 15.8 | 5.6 | 8.1 |
| 18.2 | 4.9 | 0.4 |
| 19.1 | 4.6 | 2.0 |
| 19.8 | 4.5 | 0.2 |
| 21.1 | 4.2 | 2.5 |
| 21.2 | 4.2 | 2.2 |
| 23.1 | 3.8 | 1.9 |
| 23.7 | 3.8 | 1.1 |
| 25.5 | 3.5 | 0.6 |
| 26.5 | 3.4 | 5.1 |
| 26.6 | 3.4 | 6.8 |
| 28.1 | 3.2 | 0.4 |
| 28.6 | 3.1 | 0.6 |
| 30.1 | 3.0 | 1.1 |
| 30.6 | 2.9 | 0.2 |
| 31.2 | 2.9 | 2.7 |
| 32.0 | 2.8 | 3.7 |
| 32.6 | 2.8 | 0.3 |
| 36.7 | 2.5 | 0.3 |
| 37.6 | 2.4 | 0.5 |
| 38.7 | 2.3 | 0.6 |
| 39.2 | 2.3 | 0.6 |

[Example 4] 1-{[(1,1,1,3,3,3-Hexafluoro-2-propoxy) carbonyl]oxy}ethyl (R)-isobutyrate and 1-{[(1,1,1, 3,3,3-hexafluoro-2-propoxy)carbonyl]oxy}ethyl (S)-isobutyrate

[Formula 27]

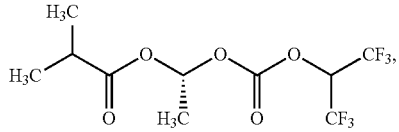

[Formula 28]

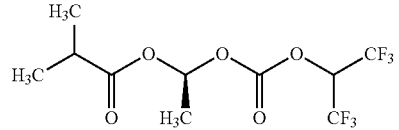

1-{[(1,1,1,3,3,3-Hexafluoro-2-propoxy)carbonyl] oxy}ethyl isobutyrate (99.3 g) as a racemate was fractionated using an HPLC optically active column (column: CHIRALCEL OJ-H, mobile phase: hexane/isopropanol=98/ 2), so as to obtain 1-{[(1,1,1,3,3,3-hexafluoro-2-propoxy) carbonyl]oxy}ethyl (R)-isobutyrate (43.0 g, 43.3%) as a first peak, and 1-{[(1,1,1,3,3,3-hexafluoro-2-propoxy)carbonyl] oxy}ethyl (S)-isobutyrate (40.2 g, 40.5%) as a second peak.

$^1$H-NMR (CDCl$_3$) δ: 6.82 (1H, q, J=5.5 Hz), 5.55 (1H, hept, J=5.5 Hz), 2.58 (1H, hept, J=7.0 Hz), 1.58 (3H, d, J=5.5 Hz), 1.18 (6H, d, J=7.0 Hz).

Optical Rotation

1-{[(1,1,1,3,3,3-Hexafluoro-2-propoxy)carbonyl] oxy}ethyl (R)-isobutyrate: $[α]_D^{25}$=+8.56 (c=1.0, CHCl$_3$)

1-{[(1,1,1,3,3,3-Hexafluoro-2-propoxy)carbonyl] oxy}ethyl (S)-isobutyrate: $[α]_D^{25}$=−8.43 (c=1.0, CHCl$_3$)

IR (ATR Method)

1-{[(1,1,1,3,3,3-Hexafluoro-2-propoxy)carbonyl] oxy}ethyl (R)-isobutyrate: 2980, 1786, 1756, 1386, 1366, 1300, 1258, 1233, 1200, 1111, 1052, 1005, 936, 899, 863, 780, 758, 709, 689, 518, and 479 cm$^{-1}$.

1-{[(1,1,1,3,3,3-Hexafluoro-2-propoxy)carbonyl] oxy}ethyl (S)-isobutyrate: 2980, 1786, 1757, 1386, 1365, 1301, 1258, 1232, 1200, 1111, 1053, 1005, 936, 899, 863, 780, 758, 710, 689, 518, and 480 cm$^{-1}$.

[Example 5] 1-{[(1,1,1,3,3,3-Hexafluoro-2-propoxy) carbonyl]oxy}ethyl (R)-isobutyrate

[Formula 29]

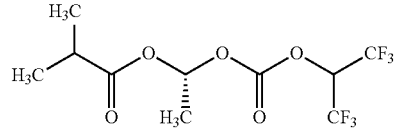

(Method 1)

A solution of potassium dihydrogen phosphate (13.5 g, 99.20 mmol) and potassium hydrogen phosphate (36.0 g, 206.67 mmol) in water (300 mL) was cooled to 20° C. Thereafter, CHIRAZYME L-2,C4 (3.0 g) was added to the reaction solution, methyl tert-butyl ether (90 mL) was then added thereto, and 1-{[(1,1,1,3,3,3-hexafluoro-2-propyloxy)

carbonyl]oxy}ethyl isobutyrate (30.00 g, 91.97 mmol) as a racemate was then added thereto. The obtained mixture was stirred at the same temperature for 38 hours. Thereafter, after confirming the completion of the reaction, methyl tert-butyl ether (60 mL) and hexane (150 mL) were added to the reaction mixture, and the enzyme was then removed by filtration. The enzyme was washed with a methyl tert-butyl ether/hexane solution (1:1, 60 mL), and the obtained mixed solution was subjected to liquid separation. Activated carbon (3.0 g) was added to the obtained organic layer, and the obtained mixture was then stirred at 20° C. for 30 minutes. After that, the activated carbon was removed by filtration. The activated carbon was washed with a methyl tert-butyl ether/hexane solution (1:1, 60 mL), and water (150 mL) was then added thereto. Using triethylamine, the aqueous layer was adjusted to pH 9.6, and the mixed solution was then subjected to liquid separation. The obtained organic layer was washed with water (300 mL) five times, and the obtained solution was then concentrated under reduced pressure to 30 mL, so as to obtain the title compound in the form of a mixed solution with hexane (HPLC quantification: 11.90 g, HPLC quantification yield: 39.7%, enantiomeric excess: 98.4% ee).

(Method 2)

A solution of potassium dihydrogen phosphate (14.4 g, 105.81 mmol) and potassium hydrogen phosphate (33.9 g, 194.62 mmol) in water (300 mL) was cooled to 20° C. Thereafter, CHIRAZYME L-2,C4 (3.0 g) was added to the reaction solution, methyl tert-butyl ether (90 mL) was then added thereto, and 1-{[(1,1,1,3,3,3-hexafluoro-2-propyloxy) carbonyl]oxy}ethyl isobutyrate (30.00 g, 91.97 mmol) as a racemate was then added thereto. The obtained mixture was stirred at the same temperature for 21 hours. Thereafter, after confirming the completion of the reaction, methyl tert-butyl ether (60 mL) and hexane (150 mL) were added to the reaction mixture, and after liquid separation, the enzyme was removed by filtration. The enzyme was washed with a methyl tert-butyl ether/hexane solution (1:1, 60 mL), and the obtained filtrate was then washed with 20% saline (300 mL). The obtained solution was concentrated under reduced pressure to 30 mL. The obtained residue was subjected to purification through distillation (degree of vacuum: 1.5 kPa, a fraction of 65° C.-55° C. was fractionated), so as to obtain the title compound in the form of a colorless oily substance (9.28 g, yield: 30.9%, enantiomeric excess: 99.4% ee).

$^1$H-NMR (500 MHz, CDCl$_3$): δ 6.82 (1H, q, J=5.5 Hz), 5.55 (1H, hept, J=5.5 Hz), 2.58 (1H, hept, J=7.0 Hz), 1.59 (3H, d, J=5.5 Hz), 1.18 (6H, d, J=7.0 Hz).

(Method 3)

CHIRAZYME L-2,C4.1 (5.0 mg) was added to a phosphate buffer (0.5 M, pH 7.0, 2.5 mL), methyl tert-butyl ether (0.5 mL) was then added thereto, and 1-{[(1,1,1,3,3,3-hexafluoro-2-propyloxy)carbonyl]oxy}ethyl isobutyrate (50 mg, 0.153 mmol) as a racemate was then added thereto. The obtained mixture was stirred at room temperature overnight. After confirming the completion of the reaction, methyl tert-butyl ether (2.0 mL) was added to the reaction mixture, and the enzyme was then removed by filtration. The obtained mixed solution was subjected to liquid separation, and was then concentrated under reduced pressure, so as to obtain the title compound in the form of a concentrated and dried product (HPLC quantification yield: 38.4%, enantiomeric excess: 99.4% ee).

(Method 4)

CHIRAZYME L-2,C3 (5.0 mg) was added to a phosphate buffer (0.5 M, pH 7.0, 2.5 mL), hexane (0.5 mL) was then added thereto, and 1-{[(1,1,1,3,3,3-hexafluoro-2-propyloxy) carbonyl]oxy}ethyl isobutyrate (50 mg, 0.153 mmol) as a racemate was then added thereto. The obtained mixture was stirred at room temperature overnight. After confirming the completion of the reaction, methyl tert-butyl ether (2.0 mL) was added to the reaction mixture, and the enzyme was then removed by filtration. The obtained mixed solution was subjected to liquid separation, and was then concentrated under reduced pressure, so as to obtain the title compound in the form of a concentrated and dried product (HPLC quantification yield: 33.4%, enantiomeric excess: 99.4% ee).

(Method 5)

CHIRAZYME L-2,CB (5.0 mg) was added to a phosphate buffer (0.5 M, pH 7.0, 2.5 mL), hexane (0.5 mL) was then added thereto, and 1-{[(1,1,1,3,3,3-hexafluoro-2-propyloxy) carbonyl]oxy}ethyl isobutyrate (50 mg, 0.153 mmol) as a racemate was then added thereto. The obtained mixture was stirred at room temperature overnight. After confirming the completion of the reaction, methyl tert-butyl ether (2.0 mL) was added to the reaction mixture, and the enzyme was then removed by filtration. The obtained mixed solution was subjected to liquid separation, and was then concentrated under reduced pressure, so as to obtain the title compound in the form of a concentrated and dried product (HPLC quantification yield: 16.2%, enantiomeric excess: 64.4% ee).

(Method 6)

CHIRAZYME L-5,CA (5.0 mg) was added to a phosphate buffer (0.5 M, pH 7.0, 2.5 mL), hexane (0.5 mL) was then added thereto, and 1-{[(1,1,1,3,3,3-hexafluoro-2-propyloxy) carbonyl]oxy}ethyl isobutyrate (50 mg, 0.153 mmol) as a racemate was then added thereto. The obtained mixture was stirred at room temperature overnight. After confirming the completion of the reaction, methyl tert-butyl ether (2.0 mL) was added to the reaction mixture, and the enzyme was then removed by filtration. The obtained mixed solution was subjected to liquid separation, and was then concentrated under reduced pressure, so as to obtain the title compound in the form of a concentrated and dried product (HPLC quantification yield: 12.0%, enantiomeric excess: 66.4% ee).

(Method 7)

CHIRAZYME L-8.1 (5.0 mg) was added to a phosphate buffer (0.5 M, pH 7.0, 2.5 mL), hexane (0.5 mL) was then added thereto, and 1-{[(1,1,1,3,3,3-hexafluoro-2-propyloxy) carbonyl]oxy}ethyl isobutyrate (50 mg, 0.153 mmol) as a racemate was then added thereto. The obtained mixture was stirred at room temperature overnight. After confirming the completion of the reaction, methyl tert-butyl ether (2.0 mL) was added to the reaction mixture, and the enzyme was then removed by filtration. The obtained mixed solution was subjected to liquid separation, and was then concentrated under reduced pressure, so as to obtain the title compound in the form of a concentrated and dried product (HPLC quantification yield: 45.3%, enantiomeric excess: 30.0% ee).

(Method 8)

Lipase AY "Amano" 30 (5.0 mg) was added to a phosphate buffer (0.5 M, pH 7.0, 2.5 mL), hexane (0.5 mL) was then added thereto, and 1-{[(1,1,1,3,3,3-hexafluoro-2-propyloxy)carbonyl]oxy}ethyl isobutyrate (50 mg, 0.153 mmol) as a racemate was then added thereto. The obtained mixture was stirred at room temperature overnight. After confirming the completion of the reaction, methyl tert-butyl ether (2.0 mL) was added to the reaction mixture, and the enzyme was then removed by filtration. The obtained mixed solution was subjected to liquid separation, and was then concentrated under reduced pressure, so as to obtain the title compound in the form of a concentrated and dried product (HPLC quantification yield: 41.3%, enantiomeric excess: 31.6% ee).

(Method 9)

Lipase AYS "Amano" (5.0 mg) was added to a phosphate buffer (0.5 M, pH 7.0, 2.5 mL), hexane (0.5 mL) was then added thereto, and 1-{[(1,1,1,3,3,3-hexafluoro-2-propyloxy)carbonyl]oxy}ethyl isobutyrate (50 mg, 0.153 mmol) as a racemate was then added thereto. The obtained mixture was stirred at room temperature overnight. After confirming the completion of the reaction, methyl tert-butyl ether (2.0 mL) was added to the reaction mixture, and the enzyme was then removed by filtration. The obtained mixed solution was subjected to liquid separation, and was then concentrated under reduced pressure, so as to obtain the title compound in the form of a concentrated and dried product (HPLC quantification yield: 41.6%, enantiomeric excess: 37.4% ee).
(Method 10)

Novozyme 435 (5.0 mg) was added to a phosphate buffer (0.5 M, pH 7.0, 2.5 mL), hexane (0.5 mL) was then added thereto, and 1-{[(1,1,1,3,3,3-hexafluoro-2-propyloxy)carbonyl]oxy}ethyl isobutyrate (50 mg, 0.153 mmol) as a racemate was then added thereto. The obtained mixture was stirred at room temperature overnight. After confirming the completion of the reaction, methyl tert-butyl ether (2.0 mL) was added to the reaction mixture, and the enzyme was then removed by filtration. The obtained mixed solution was subjected to liquid separation, and was then concentrated under reduced pressure, so as to obtain the title compound in the form of a concentrated and dried product (HPLC quantification yield: 41.1%, enantiomeric excess: 84.8% ee).
[Analysis Conditions]

In Example 5, the optical purity of 1-{[(1,1,1,3,3,3-hexafluoro-2-propyloxy)carbonyl]oxy}ethyl isobutyrate was confirmed according HPLC under the following analysis conditions.

Column: CHIRALPAK OJ-RH, 4.6 mm I.D.×150 mm (5 μm)

Mobile phase: (A) 0.1% TFA aq., (B) Acetonitrile=52/48
Column temperature: 38° C.
Flow rate: 1 mL/min
Detection: UV 215 nm
Analysis time: 8 min
Diluent: MeCN
Amount injected: 10 μL injection
Retention Time:
1-{[(1,1,1,3,3,3-hexafluoro-2-propyloxy)carbonyl]oxy}ethyl (R)-isobutyrate: 5.1 min
1-{[(1,1,1,3,3,3-hexafluoro-2-propyloxy)carbonyl]oxy}ethyl (S)-isobutyrate: 5.8 min

[Example 6] (2S)-5-({[(1R)-1-(Isobutyryloxy)ethoxy]carbonyl}amino)-2-{[1-(trans-4-methylcyclohexyl)-1H-imidazol-4-yl]methyl}valeric acid

[Formula 30]

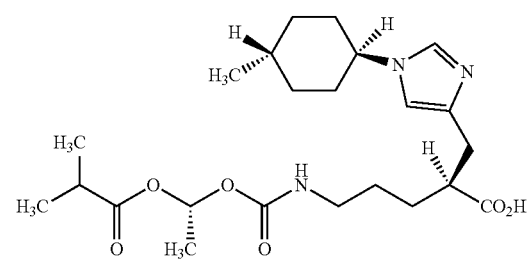

A suspension of (2S)-5-amino-2-{[1-(trans-4-methylcyclohexyl)-1H-imidazol-4-yl]methyl}valeric acid-p-toluenesulfonate-anhydride (5.0 g, 10.74 mmol) in acetonitrile (45 mL) was cooled to 0° C. Thereafter, a 25% aqueous solution of sodium hydroxide (1.72 g, 10.74 mmol), triethylamine (2.17 mL, 21.48 mmol) and 1-{[(1,1,1,3,3,3-hexafluoro-2-propyloxy)carbonyl]oxy}ethyl (R)-isobutyrate (4.20 g, 12.89 mmol) were added to the reaction solution, and the obtained mixture was then stirred at 0° C. for 20 hours. Thereafter, concentrated hydrochloric acid (1.09 g, 10.74 mmol) and a mixed solution of ethyl acetate and tetrahydrofuran (1:1, 60 mL) were added to the reaction solution, and 10% saline (30 mL) comprising concentrated hydrochloric acid (1.09 g, 10.74 mmol) was then poured into the mixture. After completion of stirring, the aqueous layer was adjusted to pH 6.8 with concentrated hydrochloric acid, followed by liquid separation. After that, the organic layer was washed with 20% saline (30 mL) six times. The obtained organic layer was concentrated under reduced pressure to 50 mL, ethyl acetate (75 mL) was then added thereto, and the obtained mixture was then concentrated under reduced pressure to 50 mL. Ethyl acetate (75 mL) was added to the residue, and the obtained mixture was then concentrated under reduced pressure to 50 mL. Thereafter, the reaction mixture was cooled to 0° C., and was then stirred for 1 hour. Thereafter, the precipitated crystals were filtrated, and the crystals were washed with cold ethyl acetate (10 mL), followed by vacuum drying, to obtain the title compound in the form of white crystals (4.09 g, yield: 84.3%).

$^1$H-NMR (CDCl$_3$) δ: 7.58 (1H, d, J=1.5 Hz), 6.78 (1H, q, J=5.5 Hz), 6.74 (1H, s), 4.98 (1H, t, J=5.5 Hz), 3.84 (1H, tt, J=12.0, 4.0 Hz), 3.22-3.11 (2H, m), 2.86 (1H, dd, J=15.0, 8.5 Hz), 2.78 (1H, dt, J=15.0, 3.0 Hz), 2.70-2.64 (1H, m), 2.52 (1H, tt, J=7.0, 7.0 Hz), 2.14-2.07 (2H, m), 1.90-1.84 (2H, m), 1.78-1.57 (5H, m), 1.49-1.41 (2H, m), 1.44 (1H, d, J=7.0 Hz), 1.15 (6H, dd, J=6.5, 0.5 Hz), 1.15-1.05 (2H, m), 0.95 (3H, d, J=6.5 Hz).

[Example 7] (2S)-5-({[(1S)-1-(Isobutyryloxy)ethoxy]carbonyl}amino)-2-{[1-(trans-4-methylcyclohexyl)-1H-imidazol-4-yl]methyl}valeric acid

[Formula 31]

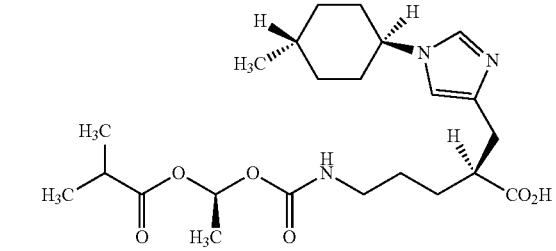

A suspension of (2S)-5-amino-2-{[1-(trans-4-methylcyclohexyl)-1H-imidazol-4-yl]methyl}valeric acid-p-toluenesulfonate-anhydride (10 g, 21.48 mmol) in acetonitrile (100 mL) was cooled to 0° C. Thereafter, 1,8-diazabicyclo[5.4.0]undec-7-ene (3.27 g, 21.48 mmol), triethylamine (4.35 g, 42.96 mmol) and 1-{[(1,1,1,3,3,3-hexafluoro-2-propoxy)carbonyl]oxy}ethyl (S)-isobutyrate (8.41 g, 25.77 mmol) were added to the reaction solution, and the obtained mixture was then stirred at 0° C. for 4 hours. Thereafter, concentrated hydrochloric acid (2.18 g, 42.96 mmol) and ethyl acetate (100 mL) were added to the reaction solution, and 10% saline (100 mL) was then poured into the mixture. After completion of stirring, the aqueous layer was adjusted to pH 6.25 with concentrated hydrochloric acid, and was then subjected to liquid separation, followed by extraction with ethyl acetate (50 mL). The obtained organic layers were combined, and the combined organic layer was then washed with 20% saline (10 mL) four times. To the obtained organic layer, water (30 mL) was added, and after completion of stirring, the aqueous layer was adjusted to pH 6.3 with concentrated hydrochloric acid and was then subjected to liquid separation. The obtained organic layer was concentrated under reduced pressure to 20 mL, and ethyl acetate (100 mL) was then added thereto. The obtained mixture was concentrated under reduced pressure to 20 mL. Ethyl acetate (100 mL) was added to the residue, and the obtained mixture was then concentrated under reduced pressure to 20 mL. Thereafter, heptane (60 mL) was added dropwise to the residue, followed by concentrating and drying, to obtain the title compound in the form of an oily compound (crude yield: 12.30 g, content: 71.0%, HPLC yield: 90.0%).

$^1$H-NMR (CDCl$_3$) δ: 7.60 (1H, d, J=1.0 Hz), 6.80 (1H, s) 6.78 (1H, q, J=5.5 Hz), 5.02 (1H, t, J=5.5 Hz), 3.87 (1H, tt, J=12.0, 3.5 Hz), 3.19-3.14 (2H, m), 2.88 (1H, dd, J=16.0, 9.0 Hz), 2.76 (1H, dt, J=16.0, 3.5 Hz), 2.70-2.64 (1H, m), 2.54 (1H, tt, J=7.0, 7.0 Hz), 2.14-2.07 (2H, m), 1.90-1.84 (2H, m), 1.78-1.57 (5H, m), 1.49-1.41 (2H, m), 1.44 (1H, d, J=5.5 Hz), 1.15 (6H, d, J=7.0 Hz), 1.15-1.05 (2H, m), 0.96 (3H, d, J=6.5 Hz).

[Analysis Conditions]

In Examples 6 and 7, the diastereomeric ratio of the product was confirmed according to HPLC under the following analysis conditions.

Column: CHIRALPAK AD-H, 4.6 mm I.D.×250 mm

Mobile phase: n-hexane/ethanol/diethylamine/acetic acid=65/35/0.1/0.1 (v/v)

Column temperature: 40° C.

Flow rate: 1 mL/min

Detection: UV 220 nm

Analysis time: 15 min

Diluent: ethanol

Amount injected: 20 μL

Retention Time:

(2S)-5-({[(1R)-1-(Isobutyryloxy)ethoxy]carbonyl}amino)-2-{[1-(trans-4-methylcyclohexyl)-1H-imidazol-4-yl]methyl}valeric acid: 6.1 min (2S)-5-({[(1S)-1-(Isobutyryloxy)ethoxy]carbonyl}amino)-2-{[1-(trans-4-methylcyclohexyl)-1H-imidazol-4-yl]methyl}valeric acid: 12.3 min

INDUSTRIAL APPLICABILITY

According to the present invention, it has been shown that a 1-(acyloxy)alkyl carbamate derivative can be produced using a fluorous alkyl carbonate derivative. It has been shown that fluorous alcohol generated as a by-product can be easily removed by a simple concentration operation, and thus that a good-quality 1-(acyloxy)alkyl carbamate derivative can be efficiently and simply produced. The production method of the present invention and a fluorous alkyl carbonate derivative used in the method are useful for the production of a 1-(acyloxy)alkyl carbamate derivative.

The invention claimed is:

1. A compound of formula (I):

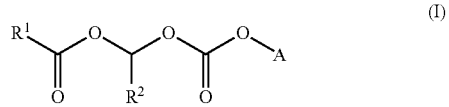

(I)

wherein R$^1$ is a C$_1$-C$_4$ alkyl group or a C$_3$-C$_6$ cycloalkyl group,
R$^2$ is a C$_1$-C$_4$ alkyl group or a hydrogen atom,
A is a fluorous alkyl group, and
the fluorous alkyl group is a C$_2$-C$_{11}$ alkyl group in which 40% or more of the hydrogen atoms are replaced by fluorine atoms.

2. The compound of claim 1, wherein the fluorous alkyl group is a 1,1,1,3,3,3-hexafluoro-2-propyl group.

3. The compound of claim 1, wherein R$^1$ is an isopropyl group and R$^2$ is a methyl group.

4. The compound of claim 1, wherein the compound is a compound of formula (VI):

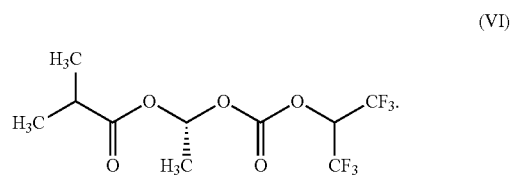 [SMILES: CC(C)C(=O)O[C@@H](C)OC(=O)OC(C(F)(F)F)C(F)(F)F]

(VI)

5. The compound of claim 1, wherein the compound is a compound of formula (VIII):

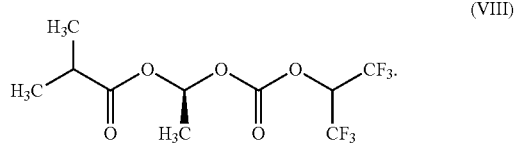 [SMILES: CC(C)C(=O)O[C@H](C)OC(=O)OC(C(F)(F)F)C(F)(F)F]

(VIII)

6. A method of producing a compound of formula (I):

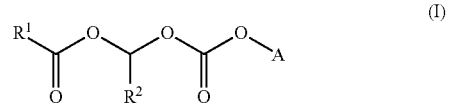

(I)

comprising allowing a compound of formula (IV):

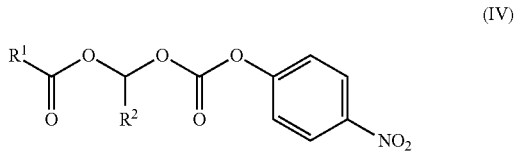

(IV)

to come into contact with a compound of formula (V):

(V)

wherein $R^1$ is a $C_1$-$C_4$ alkyl group or a $C_3$-$C_6$ cycloalkyl group, $R^2$ is a $C_1$-$C_4$ alkyl group or a hydrogen atom, A is a fluorous alkyl group, and the fluorous alkyl group is a $C_2$-$C_{11}$ alkyl group in which 40% or more of the hydrogen atoms are replaced by fluorine atoms.

7. The method of claim 6, wherein the fluorous alkyl group is a 1,1,1,3,3,3-hexafluoro-2-propyl group.

8. The method of claim 6, wherein $R^1$ is an isopropyl group and $R^2$ is a methyl group.

9. A method of producing a compound of formula (VI):

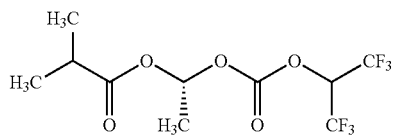

(VI)

comprising allowing a compound of formula (XI):

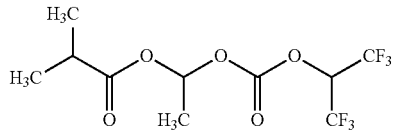

(XI)

to react with an enzyme in an inert solvent to hydrolyze a compound of formula (VIII):

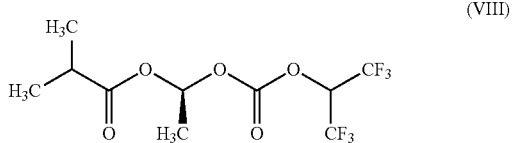 [SMILES: CC(C)C(=O)O[C@H](C)OC(=O)OC(C(F)(F)F)C(F)(F)F]

(VIII)

and then removing a product obtained by the hydrolysis, wherein the enzyme is configured to selectively hydrolyze the compound of formula (VIII).

10. The method of claim 9, wherein the enzyme is lipase derived from *Candida antarctica*, lipase derived from *Candida rugosa*, or lipase derived from *Themomyces lanuginosus*.

11. The method of claim 10, wherein the enzyme is lipase derived from *Candida antarctica*.

12. The method of claim 11, wherein the enzyme is CHIRAZYME L-2,C4.

13. The method of claim 9, wherein the inert solvent is a solvent comprising a buffer.

14. The method of claim 9, wherein the inert solvent is a solvent comprising a phosphate buffer.

* * * * *